(12) United States Patent
Hwang et al.

(10) Patent No.: US 11,744,139 B2
(45) Date of Patent: Aug. 29, 2023

(54) PHASE-TRANSITION OPTICAL ISOMER COMPOUND, TRANSPARENT ELECTROLUMINESCENT DISPLAY DEVICE AND METHOD OF FABRICATING THE TRANSPARENT ELECTROLUMINESCENT DISPLAY DEVICE

(71) Applicant: LG Display Co., Ltd., Seoul (KR)

(72) Inventors: Jun-Sik Hwang, Paju-si (KR); Nam Ki, Paju-si (KR); Chang-Woo Chun, Paju-si (KR); Eun-Ji Sim, Seoul (KR); Soo-Hyuk Choi, Seoul (KR)

(73) Assignee: LG Display Co., Ltd., Seoul (KR)

( * ) Notice: Subject to any disclaimer, the term of this patent is extended or adjusted under 35 U.S.C. 154(b) by 7 days.

(21) Appl. No.: 17/484,893

(22) Filed: Sep. 24, 2021

(65) Prior Publication Data

US 2022/0013726 A1 Jan. 13, 2022

Related U.S. Application Data

(62) Division of application No. 16/210,151, filed on Dec. 5, 2018, now Pat. No. 11,158,801.

(30) Foreign Application Priority Data

Dec. 8, 2017 (KR) .................. 10-2017-0168574

(51) Int. Cl.
*C07D 409/14* (2006.01)
*H10K 71/60* (2023.01)
(Continued)

(52) U.S. Cl.
CPC ........... *H10K 71/60* (2023.02); *C07D 409/14* (2013.01); *H10K 50/11* (2023.02); *H10K 50/16* (2023.02);
(Continued)

(58) Field of Classification Search
CPC ............. H01L 51/0021; H01L 27/3262; H01L 27/3276; H01L 51/0067; H01L 51/0068;
(Continued)

(56) References Cited

U.S. PATENT DOCUMENTS

2016/0141349 A1 5/2016 Yun et al.

FOREIGN PATENT DOCUMENTS

CN 1948424 A 4/2007
CN 101495672 A 7/2009
(Continued)

OTHER PUBLICATIONS

Tsujioka et al., "Selective Metal Deposition on Photoswitchable Molecular Surfaces," JACS Articles, Published on Web Jul. 16, 2008 from J. Am. Chem. Soc. 2008, 130, 10740-10747.
(Continued)

*Primary Examiner* — Aaron J Gray
*Assistant Examiner* — Christopher A Culbert
(74) *Attorney, Agent, or Firm* — Morgan, Lewis & Bockius LLP

(57) ABSTRACT

A phase-transition optical isomer compound is described, a transparent EL display device including the phase-transition optical isomer compound and a method of fabricating the EL display device, where a phase of the phase-transition optical isomer compound is transited by light irradiation and a second electrode of the EL display device is selectively deposited without a masking process.

8 Claims, 7 Drawing Sheets

(51) Int. Cl.
*H10K 50/11* (2023.01)
*H10K 50/16* (2023.01)
*H10K 50/17* (2023.01)
*H10K 50/813* (2023.01)
*H10K 50/822* (2023.01)
*H10K 50/844* (2023.01)
*H10K 59/131* (2023.01)
*H10K 59/121* (2023.01)
*H10K 71/00* (2023.01)
*H10K 85/60* (2023.01)
*H10K 102/00* (2023.01)

(52) U.S. Cl.
CPC ......... *H10K 50/171* (2023.02); *H10K 50/813* (2023.02); *H10K 50/822* (2023.02); *H10K 50/844* (2023.02); *H10K 59/1213* (2023.02); *H10K 59/131* (2023.02); *H10K 71/00* (2023.02); *H10K 85/654* (2023.02); *H10K 85/655* (2023.02); *H10K 85/6572* (2023.02); *H10K 85/6576* (2023.02); *H10K 59/121* (2023.02); *H10K 59/1315* (2023.02); *H10K 2102/361* (2023.02)

(58) Field of Classification Search
CPC ............. H01L 51/0072; H01L 51/0074; H01L 51/5012; H01L 51/5072; H01L 51/5092; H01L 51/5209; H01L 51/5225; H01L 51/5253; H01L 51/56; H01L 27/326; H01L 27/3279; H01L 2251/556; C07D 409/14; H10K 71/60; H10K 85/654; H10K 59/131; H10K 71/00; H10K 85/655; H10K 59/1213; H10K 50/16; H10K 50/11; H10K 85/6576; H10K 50/822; H10K 50/171; H10K 50/844; H10K 85/6572; H10K 50/813; H10K 2102/361; H10K 59/1315; H10K 59/121
See application file for complete search history.

(56) References Cited

FOREIGN PATENT DOCUMENTS

| | | |
|---|---|---|
| KR | 10-2013-0019949 A | 2/2013 |
| KR | 10-2013-0071543 A | 7/2013 |
| WO | 2009/054608 A1 | 4/2009 |
| WO | 2012/158851 A1 | 11/2012 |

OTHER PUBLICATIONS

Tsujioka, "Selective Metal-vapor Deposition on Organic Surfaces," The Chemical Record, 2016, 16, 231-248.

PHASE-TRANSITION OPTICAL ISOMER COMPOUND, TRANSPARENT ELECTROLUMINESCENT DISPLAY DEVICE AND METHOD OF FABRICATING THE TRANSPARENT ELECTROLUMINESCENT DISPLAY DEVICE

CROSS-REFERENCE TO RELATED APPLICATIONS

This application is a divisional of co-pending U.S. patent application Ser. No. 16/210,151, filed on Dec. 5, 2018, which claims the benefit of Korean Patent Application No. 10-2017-0168574, filed in the Republic of Korea on Dec. 8, 2017. All of the above applications are hereby incorporated by reference in its entirety.

BACKGROUND

Field of Technology

The present disclosure relates to an electroluminescent display device, and more particularly, to a phase-transition optical isomer compound capable of selectively depositing a conductive material without a mask process, a transparent electroluminescent display device including the phase-transition optical isomer compound and a method of fabricating the transparent electroluminescent display device.

Discussion of the Related Art

As a result of the growth of information technology and mobile communication technology, devices capable of displaying a visual image have been developed. Examples include flat panel display devices, such as liquid crystal display (LCD) devices, plasma display panel (PDP) devices, field emission display (FED) devices, and electroluminescent (EL) display devices.

Among the flat panel displays, the EL display device provides advantages, for example, in response time, viewing angle and power consumption. Accordingly, the electroluminescent display device has been widely researched and developed.

Recently, a transparent display device has been developed where light is transmitted through both a front side and a rear side such that an image is displayed that allows an unobstructed view.

FIG. 1 is a schematic cross-sectional view of a conventional art transparent EL display device.

As shown in FIG. 1, the conventional art transparent EL display device 10 includes a thin film transistor (TFT) 20 on a substrate 11 and an emitting diode (D) connected to the TFT 20.

A plurality of sub-pixel regions (SP) are defined on the substrate 11, and the TFT 20 is positioned in each sub-pixel region SP. The TFT 20 may be a driving element.

For example, the TFT 20 may include a semiconductor layer, a gate electrode, a source electrode and a drain electrode.

A passivation layer 22 is formed over an entire surface of the substrate 11 to cover the TFT 20. The passivation layer 22 includes a contact hole 24 exposing a portion of the TFT 20, e.g., a drain electrode of the TFT 20.

A first electrode 30, which is connected to the TFT 20 through the contact hole 24, is formed on the passivation layer 22. The first electrode 30 is separated in each sub-pixel region (SP).

In addition, a bank 32 covering an edge of the first electrode 30 and exposing a center of the first electrode 30 is formed on the passivation layer 22. The bank 32 is formed at a boundary of the sub-pixel region (SP).

An emitting layer 34 is formed on the first electrode 30, and a second electrode 36, which covers an entire surface of the substrate 11, is formed on the emitting layer 34. The second electrode 36 is formed by one-body in a display region including the plurality of sub-pixel regions (SP).

For example, the first electrode 30 may be formed of a transparent conductive material, e.g., indium-tin-oxide (ITO) or indium-zinc-oxide (IZO), having a relatively high work function to serve as an anode, and the second electrode 36 may be formed of a conductive material, e.g., aluminum or magnesium, having a relatively low work function to serve as a cathode.

The first and second electrodes 30 and 36 and the emitting layer 34 therebetween constitute the emitting diode (D).

In the emitting diode (D), the hole from the first electrode 30 and the electron from the second electrode 36 are combined in the emitting layer 34 such that an exciton is generated. The exciton is transited from an excited state to a stable state such that light is emitted from the emitting diode (D).

The TFT 20 as the driving element is positioned in a driving area (DA), and the emitting diode (D) is positioned in an emission area (EA). A transparent area (TA) is defined to be adjacent to the emission area (EA).

In the related art EL display device 10, the second electrode 36 is formed in the transparent area (TA) such that a transmittance of the EL display device 10 is lowered.

A masking process is required to improve the transmittance of the EL display device by removing the second electrode 36 in the transparent area (TA). However, there is a limitation of a patterning size in the masking process. In addition, since the masking process includes a step of forming a photoresist (PR) layer, a step of exposing the PR layer, a step of developing the PR layer and a step of etching the second electrode, the fabricating process of the EL display device is complicated and the production cost of the EL display device is increased.

SUMMARY

The present invention is directed to a phase-transition optical isomer compound, a transparent EL display device and a method of fabricating the transparent EL display device that substantially obviate one or more of the problems associated with the limitations and disadvantages of the related conventional art.

Additional features and advantages of the invention are set forth in the description which follows, and will be apparent from the description, or evident by practice of the invention. The objectives and other advantages of the invention are realized and attained by the features described herein as well as in the appended drawings.

To achieve these and other advantages in accordance with the purpose of the embodiments of the invention, as described herein, an aspect of the invention is a phase-transition optical isomer compound represented by:

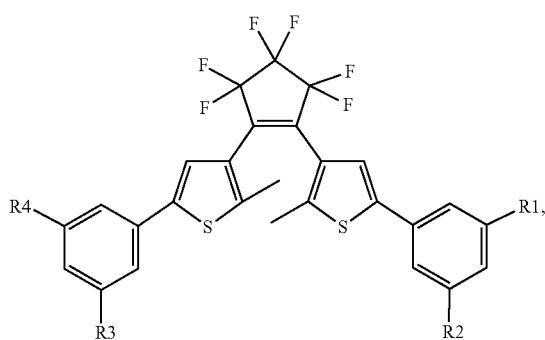

wherein each of R1 to R4 is selected from a heteroaromatic group containing a nitrogen atom.

Another aspect of the invention is a transparent electroluminescent display device including a substrate including a sub-pixel region, the sub-pixel region including an emission area and a transparent area; a first electrode over the substrate and in the emission area; an emitting material layer on the first electrode; an electron auxiliary layer on the emitting material layer and corresponding to the emission area and the transparent area; and a second electrode on the electron auxiliary layer and corresponding to the emission area.

Another aspect of the invention is a method of fabricating a transparent electroluminescent display device comprising forming a first electrode over a substrate including a sub-pixel region, wherein sub-pixel region includes an emission area and a transparent area, and the first electrode is formed in the emission area; forming an emitting material layer on the first electrode and in the emission area; forming an electron auxiliary layer on the emitting material layer and corresponding to the emission area and the transparent area, the electron auxiliary layer including a phase-transition optical isomer compound; irradiating a light onto the electron auxiliary layer in one of the emission area and the transparent area; and performing a deposition process of a conductive material onto an entire surface of the electron auxiliary layer to form a second electrode corresponding to the emission area.

It is to be understood that both the foregoing general description and the following detailed description are exemplary and explanatory and are intended to further explain the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION

Reference will now be made in detail to some of the examples and preferred embodiments, which are illustrated in the accompanying drawings.

Figure 1:
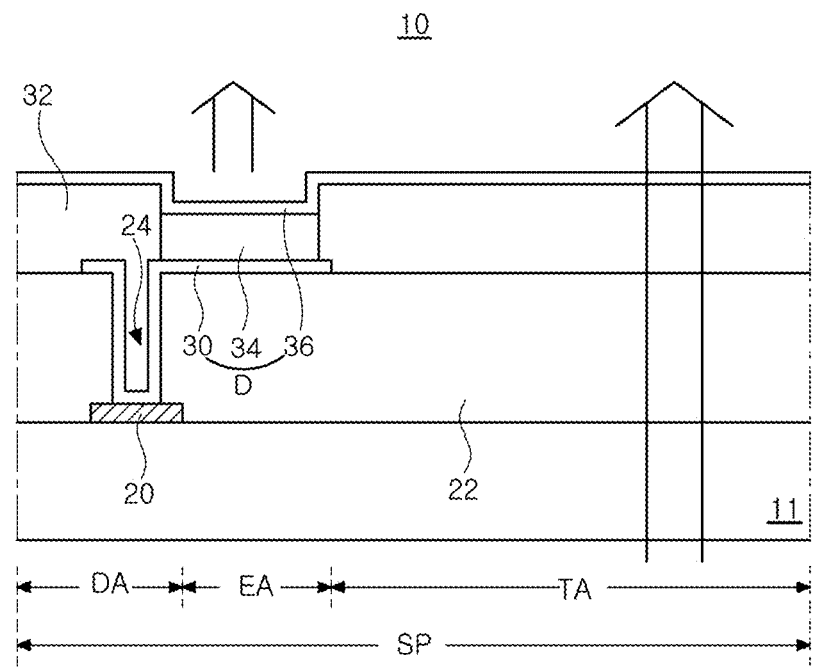
FIG. 1 is a schematic cross-sectional view of a transparent EL display device of the conventional art.
Figure 2:
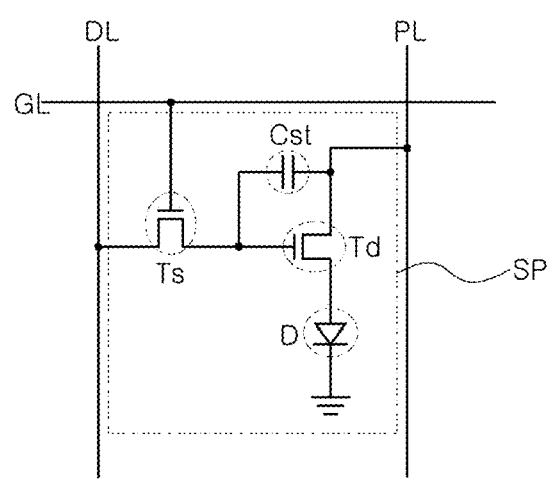
FIG. 2 is a schematic circuit diagram of a transparent EL display device of the present invention.

FIG. 2 is a schematic circuit diagram of a transparent EL display device of the present invention.

As shown in FIG. 2, a transparent EL display device includes a gate line (GL), a data line (DL), a power line (PL), a switching thin film transistor TFT (Ts), a driving TFT (Td), a storage capacitor (Cst), and an emitting diode (D). The gate line (GL) and the data line (DL) cross each other to define a sub-pixel region (SP).

Although not shown, the sub-pixel region (SP) includes an emission area and a transparent area.

The switching TFT (Ts) is connected to the gate line (GL) and the data line (DL), and the driving TFT (Td) and the storage capacitor (Cst) are connected to the switching TFT (Ts) and the power line (PL). The emitting diode (D) is connected to the driving TFT (Td).

When the switching TFT (Ts) is turned on by a gate signal applied through the gate line (GL), a data signal from the data line (DL) is applied to the gate electrode of the driving TFT (Td) and an electrode of the storage capacitor (Cst). When the driving TFT (Td) is turned on by the data signal, an electric current is supplied to the emitting diode (D) from the power line (PL). As a result, the emitting diode (D) emits light. In this case, when the driving TFT (Td) is turned on, a level of an electric current applied from the power line (PL) to the emitting diode (D) is determined such that the emitting diode (D) can produce a gray scale.

The storage capacitor (Cst) serves to maintain the voltage of the gate electrode of the driving TFT (Td) when the switching TFT (Ts) is turned off. Accordingly, even if the switching TFT (Ts) is turned off, a level of an electric current applied from the power line (PL) to the emitting diode (D) is maintained to next frame.

As a result, the transparent EL display device displays a desired image.

Figure 3:
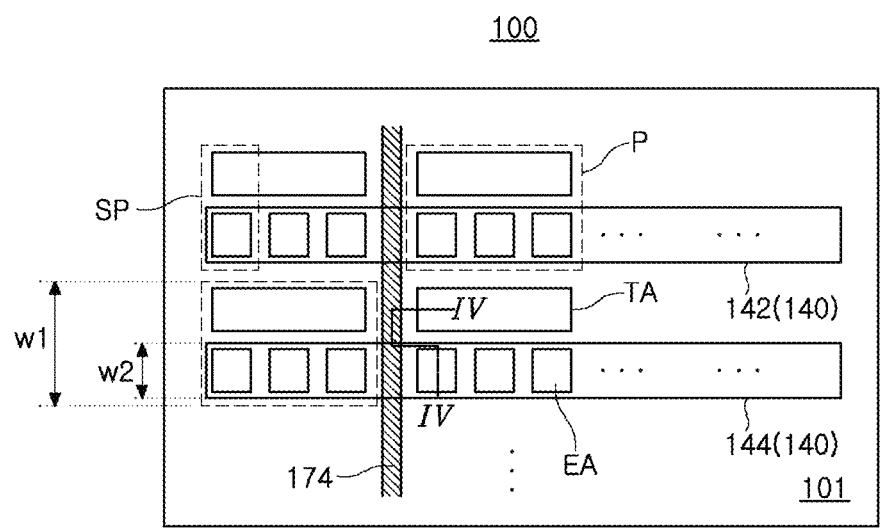
FIG. 3 is a schematic planar view of a transparent EL display device according to an embodiment of the present invention.

FIG. 3 is a schematic plane view of a transparent EL display device according to a first embodiment of the present invention.

As shown in FIG. 3, the transparent EL display device 100 includes a plurality of sub-pixel regions (SP) defined on a substrate 110 and arranged along a first direction and a second direction. Each of the plurality of sub-pixel regions (SP) includes an emission area (EA) and a transparent area (TA). Each sub-pixel region (SP) further includes a driving area (not shown).

For example, some of the plurality of sub-pixel regions (SP) arrange along the first direction may constitute a pixel region (P). The pixel region (P) may include red, green and blue sub-pixel regions (SP).

In the emission area (EA) of the sub-pixel region (SP), an emitting diode (not shown) is disposed. For example, the emitting diode may include a first electrode, an emitting layer, an electron auxiliary layer and a second electrode 140.

As described below, the electron auxiliary layer includes a phase-transition optical isomer compound and transfers an electron from the second electron 140 into the emitting layer.

Since a conductive material for the second electrode 140 is capable of being selectively deposited due to the electron auxiliary layer, the second electrode 140 is deposited in a desired area without a masking process.

The second electrode 140 corresponds to the emission area (EA) of the pixel regions (P) arranged along the first direction. Namely, in each pixel region (P) or each sub-pixel region (SP), the second electrode 140 is formed in the emission area (EA) except the transparent area (TA). Accordingly, the sub-pixel region (SP) has a first width (w1) in the second direction, and the second electrode 140 has a second width (w2), which is smaller than the first width (w1), in the second direction.

The second electrode 140 includes a plurality of electrode patterns 142 and 144 spaced apart from each other along the second direction. Namely, a first electrode pattern 142 corresponds to a first pixel row, and a second electrode pattern 144 corresponds to a second pixel row being spaced apart from the first pixel row along the second direction.

Accordingly, in the second direction, the sub-pixel region (SP) has the first width (w1), and each of the first and second electrode patterns 142 and 144 has the second width (w2) being smaller than the first width (w1).

A connection line 174 for electrically connecting the first and second electrode patterns 142 and 144 may be formed between the pixel regions (P) arranged along the first direction. Namely, the second electrodes 140, which respectively correspond to the first and second pixel rows and are spaced apart from each other, may be electrically connected to each other by the connection line 174.

In the transparent EL display device 100 of the present disclosure, since the second electrode 140 is not presented in the transparent area (TA) of the sub-pixel region (SP) and the pixel region (P), the problem of the transmittance decrease in the display area by the second electrode is prevented.

In addition, since the second electrode 140 is selectively formed in the emission area (EA) except the transparent area (TA) by the electron auxiliary layer, which includes the phase-transition optical isomer compound, without a masking process, the problems of the fabricating process and the production cost are prevented.

Moreover, since the second electrodes 140 spaced apart from each other are electrically connected by the connection line 174, there is no problem in applying voltage to the second electrodes 140.

Figure 4:
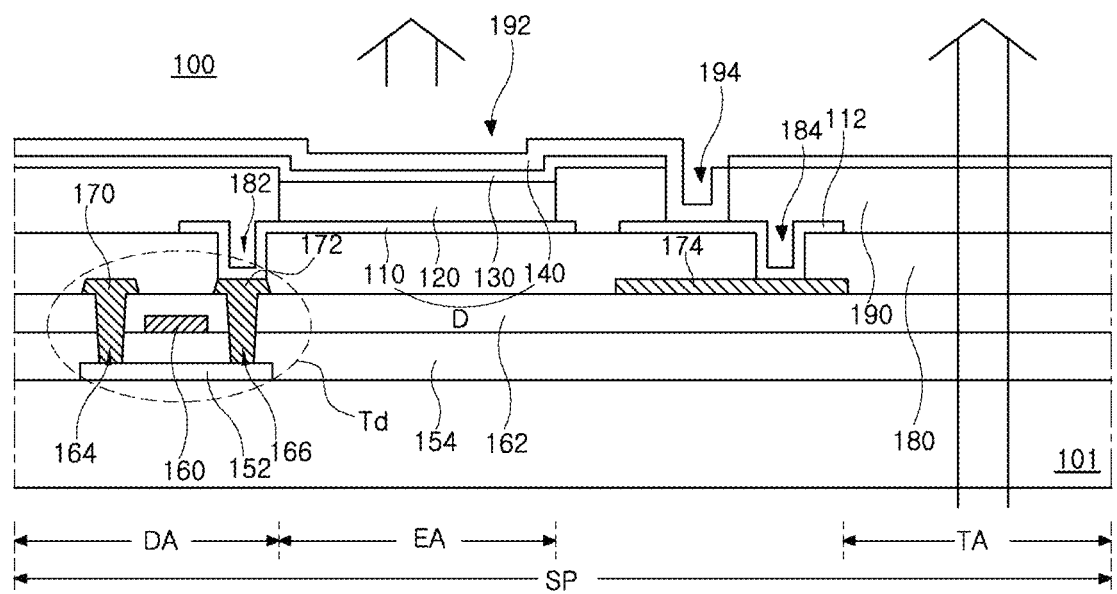
FIG. 4 is a cross-sectional view taken along the line IV-IV in FIG. 3.

FIG. 4 is a cross-sectional view taken along the line IV-IV in FIG. 3.

As shown in FIG. 4, the transparent EL display device 100 includes the substrate 101, where the sub-pixel region (SP) including the driving area (DA), the emission area (EA) and the transparent area (TA) is defined, the TFT (Td) on the substrate 101, the emitting diode (D) connected to the TFT (Td) and the connection line 174 positioned between adjacent pixel regions (P) (of FIG. 3).

The TFT (Td) is positioned in the driving area (DA) and may be a driving TFT.

The substrate 101 may be a glass substrate or a plastic substrate. For example, the substrate 101 may be a polyimide substrate.

A semiconductor layer 152 is formed on the substrate 101. The semiconductor layer 152 may include an oxide semiconductor material or polycrystalline silicon. When the semiconductor layer 152 includes the oxide semiconductor material, a light-shielding pattern (not shown) may be formed under the semiconductor layer 152. The light to the semiconductor layer 152 may be shielded or blocked by the light-shielding pattern such that thermal degradation of the semiconductor layer 152 can be prevented. When the semiconductor layer 152 includes polycrystalline silicon, impurities may be doped into both sides of the semiconductor layer 152.

Although not shown, a buffer layer may be formed under the semiconductor layer 152 and on the substrate 101. The buffer layer may be formed of an inorganic insulating material such as silicon oxide or silicon nitride.

A gate insulating layer 154 is formed over an entire surface of the substrate 101 including the semiconductor layer 152. The gate insulating layer 154 may be formed of an inorganic insulating material such as silicon oxide or silicon nitride.

A gate electrode 160, which is formed of a conductive material, e.g., a metal, is formed on the gate insulating layer 154 above a center of the semiconductor layer 152. Although not shown, the gate line (GL) (of FIG. 2) and a first capacitor electrode of the storage capacitor (Cst) (of FIG. 2) may be formed on the gate insulating layer 154. The gate line (GL) may extend along a first direction, and the first capacitor electrode may be connected to the gate electrode 160.

In FIG. 4, the gate insulating layer 154 is formed on the entire surface of the substrate 101. Alternatively, the gate insulating layer 154 may be patterned to have the same shape or a similar shape as the gate electrode 160.

An interlayer insulating layer 162, which is formed of an insulating material, is formed on an entire surface of the substrate 101 including the gate electrode 160. The interlayer insulating layer 162 may be formed of an inorganic insulating material, e.g., silicon oxide or silicon nitride, or an organic insulating material, e.g., benzocyclobutene or photo-acryl.

The interlayer insulating layer 162 includes first and second contact holes 164 and 166 exposing both sides of the semiconductor layer 152. The first and second contact holes 164 and 166 are positioned at both sides of the gate electrode 160 to be spaced apart from the gate electrode 160.

In FIG. 4, the first and second contact holes 164 and 166 extend into the gate insulating layer 154. Alternatively, when the gate insulating layer 154 is patterned to have the same shape as the gate electrode 160, the first and second contact holes 164 and 166 are formed only through the interlayer insulating layer 162 and not through the gate insulating layer 154.

A source electrode 170 and a drain electrode 172, which are formed of a conductive material, e.g., a metal, are formed on the interlayer insulating layer 162. In addition, the data line (DL) (of FIG. 2), the power line (PL) (of FIG. 2) and a second capacitor electrode (not shown) of the storage capacitor (Cst) may be formed on the interlayer insulating layer 162.

The source electrode 170 and the drain electrode 172 are spaced apart from each other with respect to the gate electrode 160 and respectively contact both sides of the semiconductor layer 152 through the first and second contact holes 164 and 166. The data line (DL) may extend along a second direction to define the sub-pixel region (SP), and the power line (PL) providing a high potential voltage may be parallel to and spaced apart from the data line (DL). Alternatively, the power line (PL) may be formed at the same layer as the gate line (GL) to be parallel to and spaced apart from the gate line (GL) such that the power line (PL) may cross the data line (DL). The second capacitor electrode may be connected to the source electrode 170 and overlap the first capacitor electrode such that the storage capacitor (Cst)

including the first and second capacitor electrodes and the interlayer insulating layer 162 as a dielectric layer therebetween is provided.

The semiconductor layer 152, the gate electrode 160, the source electrode 170 and the drain electrode 172 constitute the TFT (Td) serving as a driving element (driving TFT). In the driving TFT (Td), the gate electrode 160, the source electrode 170 and the drain electrode 172 are positioned over the semiconductor layer 152. Namely, the driving TFT (Td) has a coplanar structure.

Alternatively, in the driving TFT (Td), the gate electrode may be positioned under the semiconductor layer, and the source and drain electrodes may be positioned over the semiconductor layer such that the driving TFT (Td) may have an inverted staggered structure. In this instance, the semiconductor layer may include amorphous silicon.

As mentioned above, the switching TFT (Ts) may be further formed on the substrate 101. The switching TFT (Ts) may have substantially the same structure as the driving TFT (Td).

The gate electrode 160 of the driving TFT (Td) may be connected to a drain electrode of the switching TFT (Ts), and the source electrode 170 of the driving TFT may be connected to the power line (PL). In addition, a gate electrode and a source electrode of the switching TFT (Ts) may be connected to the gate line (GL) and the data line (DL), respectively.

The connection layer 174 is also formed on the interlayer insulating layer 162. The connection layer 174 is positioned between adjacent pixel regions (P) in the first direction and extend along the second direction. For example, the connection line 174 may be parallel to the data line (DL) and formed of the same material as the source electrode 170 and/or the data line (DL).

A passivation layer 180, which includes a drain contact hole 182 exposing the drain electrode 172 of the driving TFT (Td) and a first connection contact hole 184 exposing the connection line 174, is formed to cover the driving TFT (Td) and the connection line 174.

A first electrode 110, which is connected to the drain electrode 172 of the driving TFT (Td) through the drain contact hole 182, is separately formed in each sub-pixel region (SP). The first electrode 110 is positioned in the emission area (EA).

The first electrode 110 may be an anode and may be formed of a conductive material having a relatively high work function. For example, the first electrode 110 may be formed of a transparent conductive material such as indium-tin-oxide (ITO) or indium-zinc-oxide (IZO).

A reflection electrode or a reflection layer may be formed under the first electrode 110. For example, the reflection electrode or the reflection layer may be formed of aluminum-palladium-copper (APC) alloy.

In addition, a connection pattern 112 corresponding to a space between adjacent pixel regions (P) in the first direction is formed on the passivation layer 180. The connection pattern 112 is connected to the connection line 174 through the first connection contact hole 184. The connection pattern 112 may be formed of the same material as the first electrode 110.

A bank 190 surrounding the sub-pixel region (SP) is formed on the passivation layer 180. Namely, the bank 190 covers edges of the first electrode 110.

The bank 190 includes an opening 192 exposing the emission area (EA) in each sub-pixel region (SP) and a second connection contact hole 194 exposing the connection pattern 112.

An emitting material layer 120 is formed in the opening 192 of the bank 190. Namely, the emitting material layer 120 is formed on the first electrode 110 in the emission area (EA). The emitting material layer 120 may include an organic emitting material, e.g., a phosphorescent compound or a fluorescent compound, or an inorganic emitting material, e.g., a quantum dot.

Although not shown, a hole auxiliary layer may be formed between the first electrode 110 and the emitting material layer 120. For example, the hole auxiliary layer may include at least one of a hole transporting layer and a hole injection layer.

The electron auxiliary layer 130 is formed over an entire surface of the substrate 101 including the emitting material layer 120 except the second connection contact hole 194. Namely, the electron auxiliary layer 130 is formed in both of the emission area (EA) and the transparent area (TA) and is not presented on the second connection contact hole 194. For example, the electron auxiliary layer 130 in the second connection contact hole 194 may be etched in a step of forming the second connection contact hole 194 such that the electron auxiliary layer 130 may be formed in an entire display area except the second connection contact hole 194.

The electron auxiliary layer 130 contacts the emitting material layer 120 in the emission area (EA) and the bank 190 in the transparent area (TA). Alternatively, when the bank 190 in the transparent area (TA) is omitted, the electron auxiliary layer 130 may contact an element, e.g., the passivation layer 180, under the bank 190.

The electron auxiliary layer 130 includes a compound represented by Formula 1.

[Formula 1]

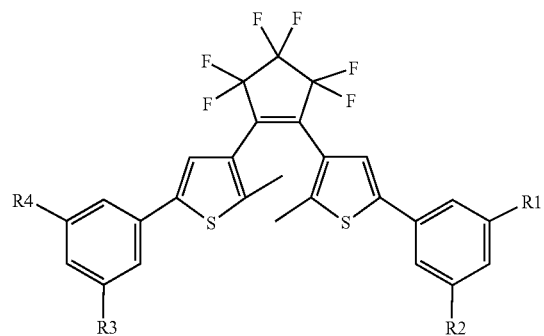

In Formula 1, each of R1 to R4 is independently selected from a heteroaromatic group containing a nitrogen atom. For example, each of R1 to R4 may be independently selected from pyridyl (pyridinyl) or quinolinyl. R1 to R4 may be same or different from one another.

For example, the compound in Formula 1 may be one of compounds 1, 2, 3 or 4 in Formula 2.

[Formula 2]
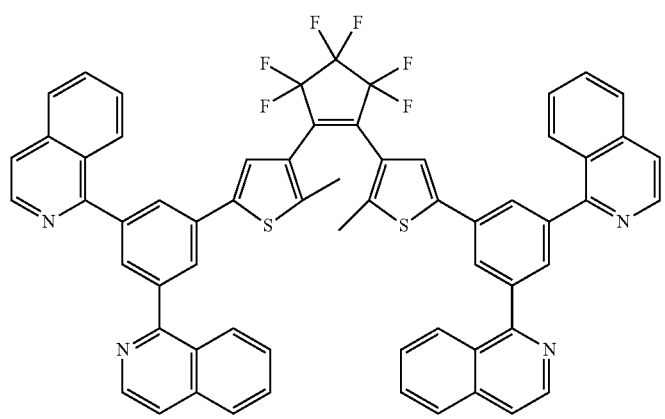
compound 1
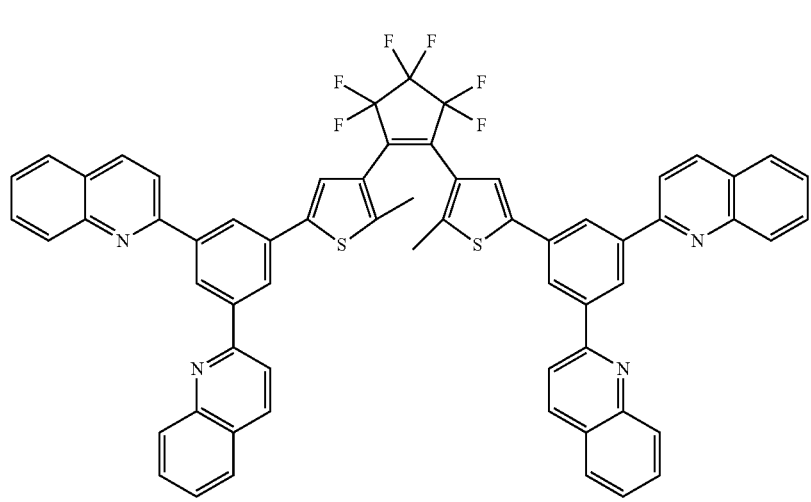
compound 2
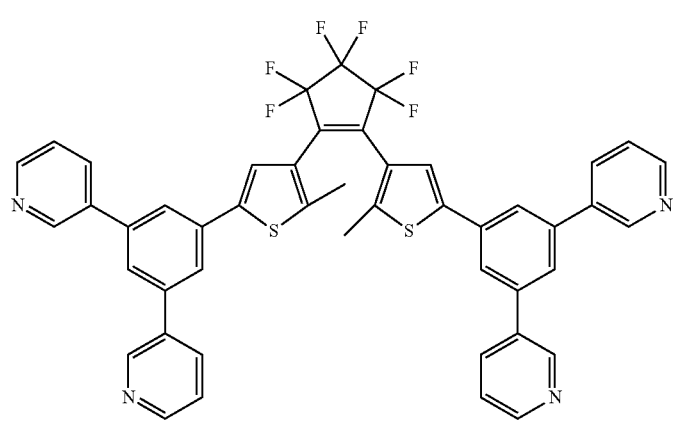
compound 3 compound 4

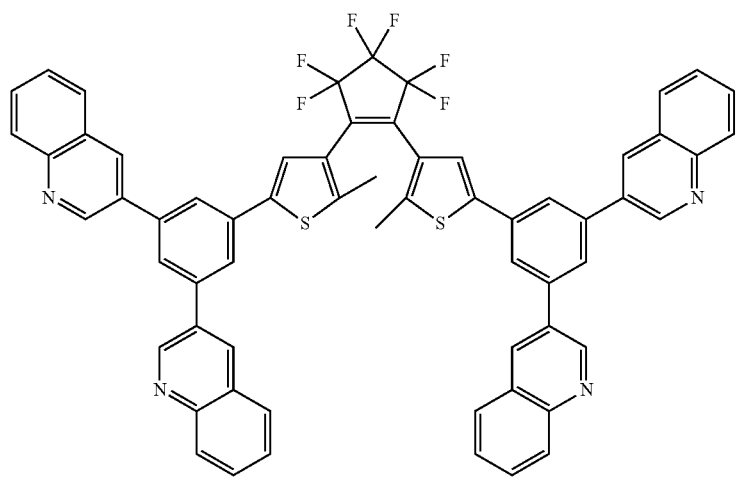

Synthesis
Synthesis of Compound 3
(1) Compound A

[Reaction Formula 1-1]

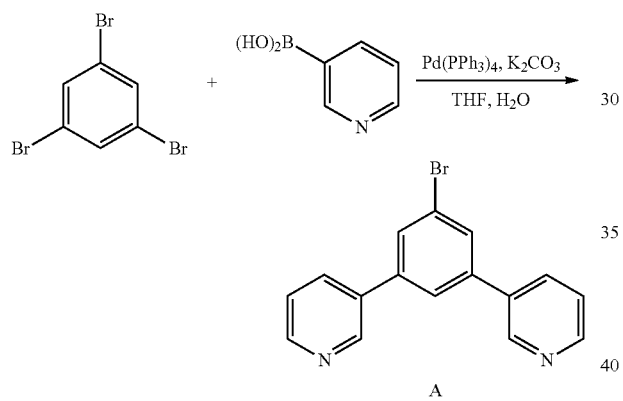

After 1,3,5-tribromobenzene (1 equivalent) and a magnetic stirring bar were introduced into a three-neck round bottom flask, tetrahydrofuran and water (3:1) were added. After $K_2CO_3$ (4 equivalents) was added and stirred for 10 minutes, $Pd(PPh_3)_4$ (0.1 equivalents) was added. 3-Pyridineboronic acid (2.1 equivalents) was added to the mixture and then stirred at a temperature of 85 to 90° C. for 1 day. After completion of the reaction, the mixture was diluted by adding ethyl acetate and cleaned by using water and brine. The solvent was then removed from the organic portion by a vacuum rotary distiller, and the resultant was separated by flash column chromatography such that Compound A was obtained. (yield: 70-80%)

(2) Compound B

[Reaction Formula 1-2]

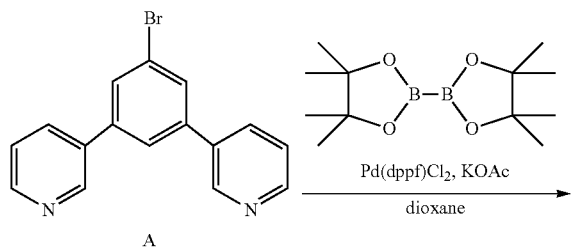

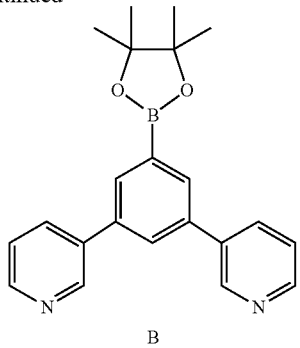

Compound A (1 equivalent) and a magnetic stirring bar were introduced into a round bottom flask. After the mixture was dissolved in anhydrous dioxane, bis(pinacolato)diboron (1.2 equivalents), $Pd(dppf)Cl_2$ (0.03 equivalents), KOAc (potassium acetate) (3.4 equivalents) were added. The mixture was stirred at a temperature of 100° C. for 1 day. After completion of the reaction, the mixture was diluted by adding ethyl acetate and cleaned by using water and brine. The solvent was then removed from the organic portion by a vacuum rotary distiller, and the resultant was separated by flash column chromatography such that Compound B was obtained. (yield: 60-70%)

(3) Compound 3

[Reaction Formula 1-3]

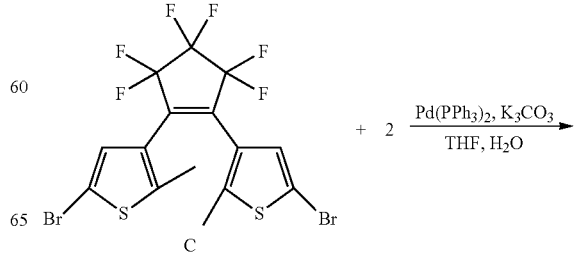

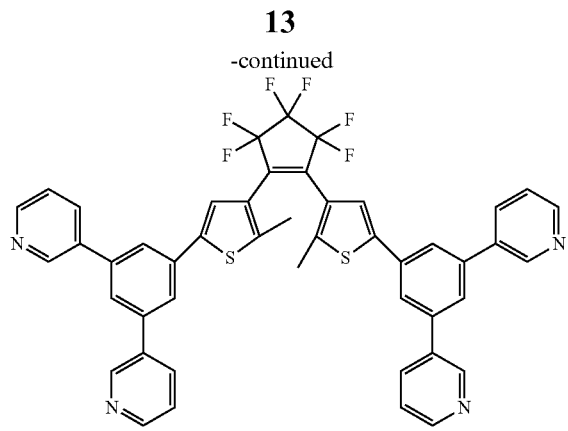

Figure 5:
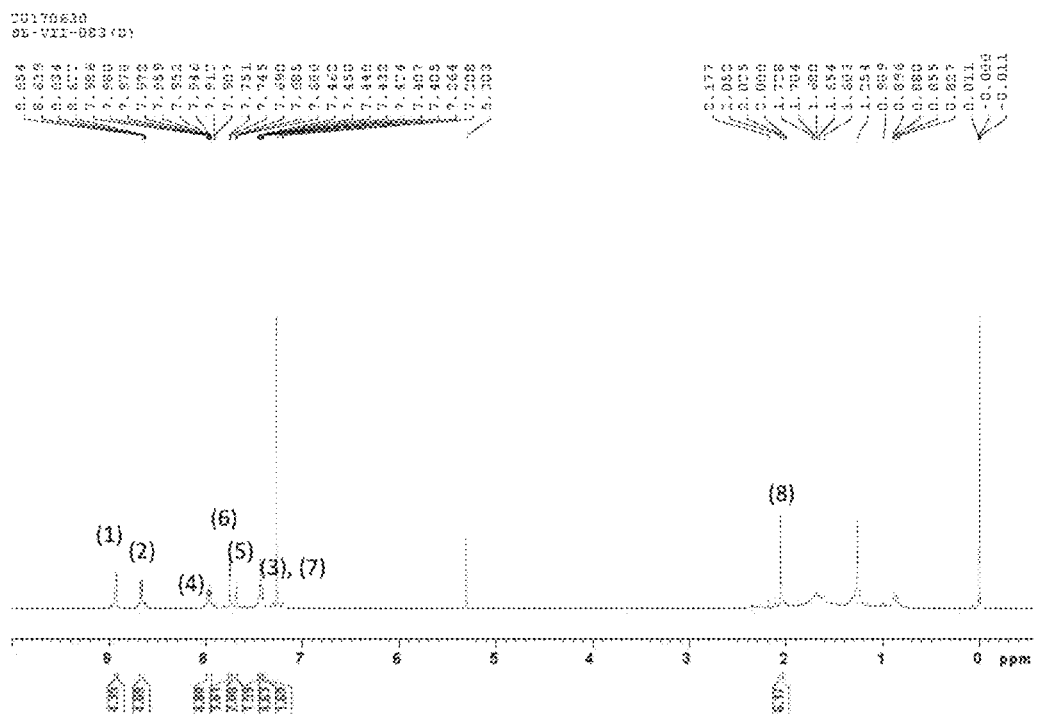
FIG. 5 is an NMR graph of compound 3.

After Compound C (1 equivalent) and Compound B (2.2 equivalents) were introduced into a round bottom flask, the mixture was dissolved in anhydrous THF. The mixture was stirred for 10 minutes with a magnetic stirring bar, and Pd(PPh$_3$)$_4$ (0.2 equivalents) and a 2 M K$_2$CO$_3$ aqueous solution (4 equivalents) were added. The mixture was then refluxed at a temperature of 85° C. for 15 to 17 hrs before being cooled to room temperature. After water was added to the mixture, the mixture was extracted with ethyl acetate. The solvent was then removed from the organic portion by a vacuum rotary distiller, and the resultant was separated by flash column chromatography such that the Compound 3 was obtained. (yield: 50%). The NMR data of Compound 3 is shown in FIG. 5.

Synthesis of Compound 4
(1) Compound D

[Reaction Formula 2-1]

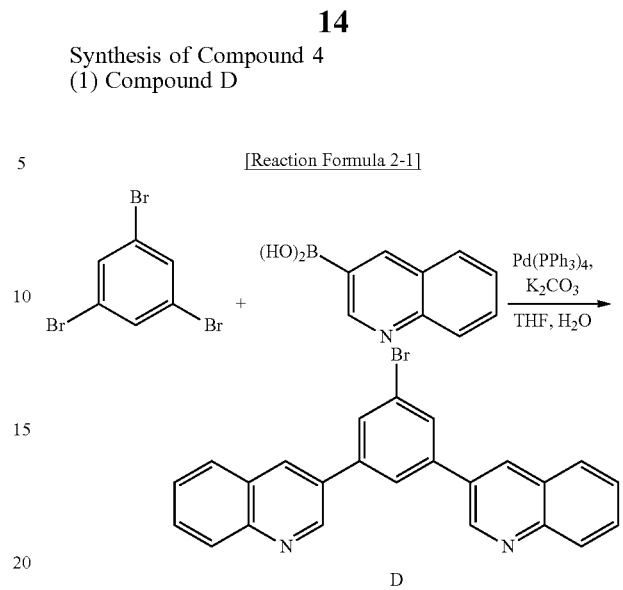

After 1,3,5-tribromobenzene (1 equivalent) and a magnetic stirring bar were introduced into a three-neck round bottom flask, tetrahydrofuran and water (3:1) were added. After K$_2$CO$_3$ (4 equivalents) was added and stirred for 10 minutes, Pd(PPh$_3$)$_4$ (0.1 equivalent) was added. 3-quinoline-boronic acid (2.1 equivalents) was then added to the mixture and stirred at a temperature of 85 to 90° C. for 1 day. After completion of the reaction, the mixture was diluted by adding ethyl acetate and cleaned by using water and brine. The solvent was then removed from the organic portion by a vacuum rotary distiller, and the resultant was separated by flash column chromatography such that Compound D was obtained. (yield: 30-50%)

(2) Compound E

[Reaction Formula 2-2]

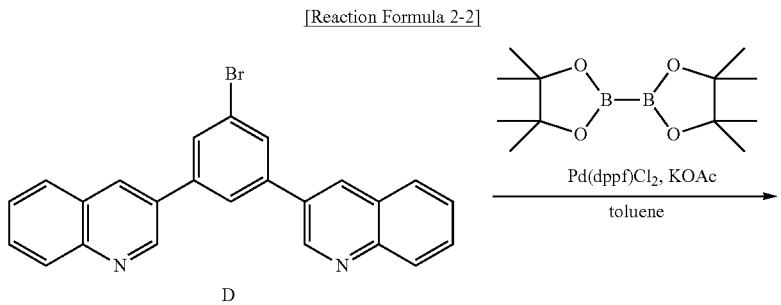

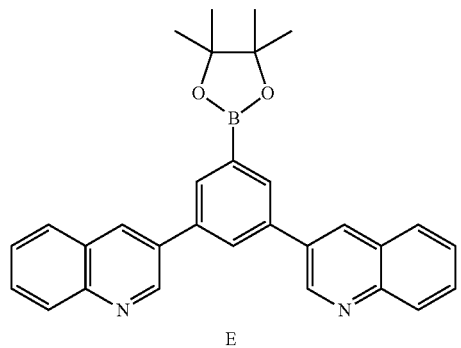

Compound D (1 equivalent) and a magnetic stirring bar were introduced into a round bottom flask. After the mixture was dissolved in anhydrous dioxane, bis(pinacolato)diboron (1.2 equivalents), Pd(dppf)Cl$_2$ (0.02 equivalents) and KOAc (potassium acetate) (3 equivalents) were added. The mixture was then stirred at a temperature of 110° C. for 1 day. After completion of the reaction, the mixture was diluted by adding ethyl acetate and cleaned by using water and brine. The solvent was removed from the organic portion by a vacuum rotary distiller, and the resultant was separated by flash column chromatography such that the compound E was obtained. (yield: 40-50%)

(3) Compound 4

[Reaction Formula 2-3]

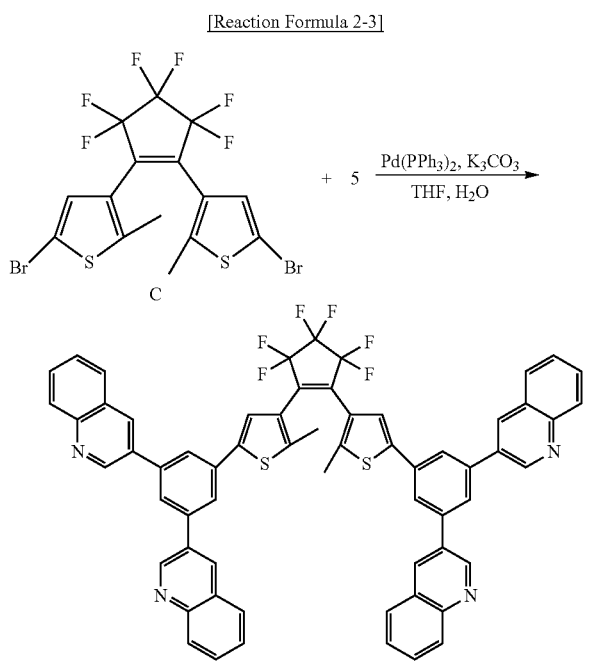

Figure 6:
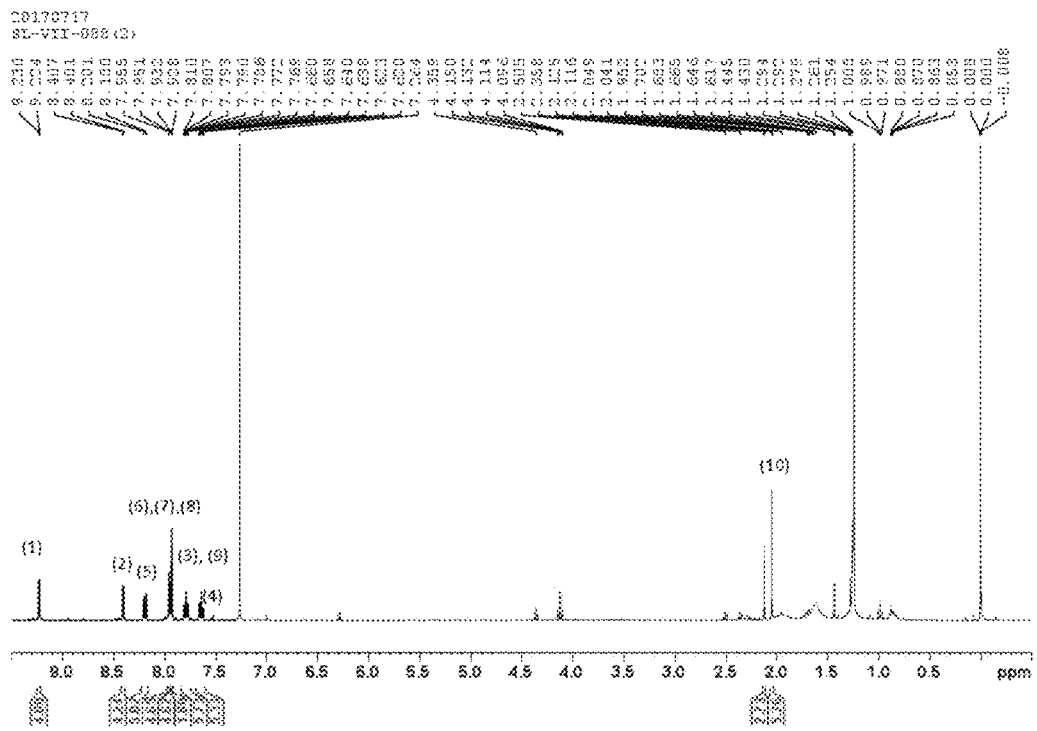
FIG. 6 is an NMR graph of compound 4.

After compound C (1 equivalent) and compound E (2.2 equivalents) were introduced into a round bottom flask, the mixture was dissolved in anhydrous THF. The mixture was stirred for 10 minutes with a magnetic stirring bar, and Pd(PPh$_3$)$_4$ (0.4 equivalents) and a 2 M K$_2$CO$_3$ aqueous solution (4 equivalents) were added. The mixture was refluxed under the temperature of 85° C. for 15 to 17 hrs before being cooled to room temperature. After water was added to the mixture, the mixture was extracted with ethyl acetate. The solvent was removed from the organic portion by a vacuum rotary distiller, and the resultant was separated by flash column chromatography such that the compound 4 was obtained. (yield: 20%). The NMR data of compound 4 is shown in FIG. 6.

A phase of a compound of Formula 1 is transited by light irradiation. The compound may therefore be referred to as a phase-transition optical isomer compound.

Figure 7:
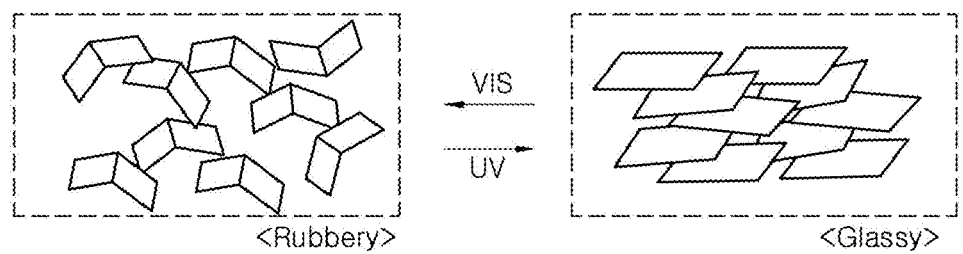
FIG. 7 is a schematic view illustrating a phase-transition mechanism of a phase-transition optical isomer compound.

Referring to FIG. 7, which is a schematic view illustrating a phase-transition mechanism of an exemplary phase-transition optical isomer compound, when the visible light ("VIS") irradiates the phase-transition optical isomer compound, the phase-transition optical isomer compound exhibits a rubbery phase. When the ultraviolet ray ("UV") irradiates the phase-transition optical isomer compound, the phase-transition optical isomer compound exhibits a glassy phase. In other words, when visible light ("VIS") is used for the irradiation, the glass temperature (Tg) of the phase-transition optical isomer compound is decreased such that the phase-transition optical isomer compound has a rubbery phase. In contrast, when ultraviolet rays ("UV") are used for the irradiation, the glass temperature of the phase-transition optical isomer compound is increased such that the phase-transition optical isomer compound has a glassy phase.

For example, the compound 1 in Formula 2 has a rubbery phase. A ring of Compound 1 is closed upon exposure to ultraviolet rays such that Compound 1 is changed into a compound of Formula 3 below (glassy phase).

[Formula 3]

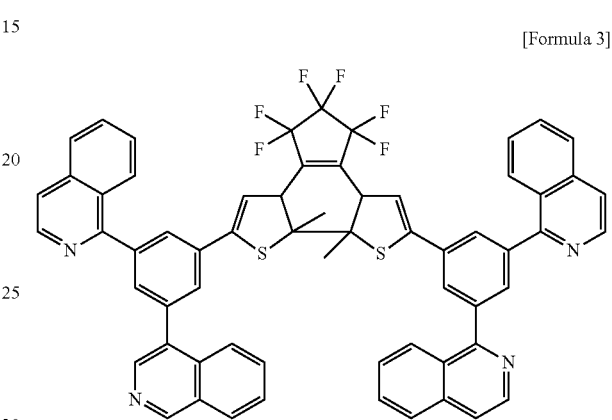

In contrast, when visible light is used for irradiating the compound of Formula 3, the ring is opened such that the compound is changed to the rubbery phase as Compound 1.

When the phase-transition optical isomer compound is in a glassy phase, a metal is deposited on a layer that includes the phase-transition optical isomer compound. In contrast, when the phase-transition optical isomer compound is in a rubbery phase, a metal is not deposited on the layer that includes the phase-transition optical isomer compound.

In the rubbery phase of the phase-transition optical isomer compound, the molecular motion is activated such that a metal atom rebounds from a surface of the phase-transition optical isomer compound layer or diffusion of the metal atom is disturbed (blocked). As a result, the generation of a crystal nucleus is blocked, and the metal is not deposited on the phase-transition optical isomer compound layer. In contrast, in the glassy phase of the phase-transition optical isomer compound, molecular motion is restricted such that deposition of the metal is not disturbed.

Accordingly, when the light, (e.g., the ultraviolet or visible rays), are used to irradiate a portion of the electron auxiliary layer 130 that includes the phase-transition optical isomer compound, the metal is deposited or not deposited in the portion of the electron auxiliary layer 130.

In addition, since the phase-transition optical isomer compound of the present disclosure has a lowest unoccupied molecular orbital (LUMO) level of about −2.6 to −2.1 eV and a highest occupied molecular orbital (HOMO) level of −6.2 to −6.0 eV, the phase-transition optical isomer compound is used in the electron auxiliary layer 130. For example, the electron injection property and/or the electron transporting property into the emitting material layer 120 is improved by the electron auxiliary layer 130 that includes the phase-transition optical isomer compound.

Moreover, in the phase-transition optical isomer compound of Formula 1 and/or Formula 2, a difference in the glass temperature between the glassy phase and the rubbery phase is in a range of about 100 to 300° C., and preferably about 200 to 300° C. For example, Compound 1 may have the glass temperature of about 140° C. in the rubbery phase and the glass temperature of about 400° C. in the glassy phase.

When the glass temperature difference in the rubbery phase and the glassy phase is smaller or greater than the above range, selectivity between the glassy phase and the rubbery phase is decreased such that there may be a problem in the selective deposition of the metal.

The second electrode 140 is formed on the electron auxiliary layer 130. In the sub-pixel region (SP) and/or the pixel region (P), the second electrode 140 covers the emission area (EA) and exposes the transparent area (TA). Namely, in the sub-pixel region (SP), the second electrode 140 has an area smaller than that of the electron auxiliary layer 130 and greater than that of the emitting material layer 120.

The second electrode 140 may be an cathode and may be formed of a conductive material having a relatively low work function. For example, the second electrode 140 may include Ag, Mg, Al and their alloys such as MgAg or AlMg.

A portion of the second electrode 140 is connected to the connection pattern 112 through the second connection contact hole 194. Namely, the second electrode 140 is electrically connected to the connection line 174 through the connection pattern 112. Accordingly, the second electrodes 140, which are spaced apart from each other, are electrically connected through the connection line 174.

In FIG. 4, the second electrode 140 and the connection line 174 are connected to each other through the connection pattern 112. Alternatively, the second electrode 140 may contact the connection line 174 without the connection pattern 112. In addition, an auxiliary line may be formed under the connection line 174, and the connection line 174 may be connected to the auxiliary line.

The connection line 174 is formed at the same layer and formed of the same material as the source electrode 170. Alternatively, the connection line 174 may be formed at the same layer and formed of the same material as other element of the driving TFT Td.

As mentioned above, the electron auxiliary layer 130 includes the phase-transition optical isomer compound. Accordingly, by using the selective deposition of the metal depending on the light irradiation, the second electrode 140 exposing the transparent area (TA) is selectively formed in the emission area (EA) without a masking process.

In the emission area (EA), the first electrode 110, the emitting material layer 120, the electron auxiliary layer 130 and the second electrode 140 constitute the emitting diode (D).

Although not shown, a cover layer may further be formed to cover the emitting diode (D). In this instance, the cover layer contacts the second electrode 140 in the emission area (EA) and contacts the electron auxiliary layer 130 in the transparent area (TA).

The cover layer is disposed on the emitting diode (D) and covers the emitting diode (D). There is no limitation in the type of cover layer suitable for use.

For example, the cover layer may be an inorganic layer or an organic layer for preventing the penetration of outer moisture. When an encapsulation substrate is attached onto the emitting diode (D) by an adhesive layer, the cover layer may be the adhesive layer.

FIGS. 8A to 8G are schematic cross-sectional views showing a fabricating process of a transparent EL display device according to the first embodiment of the present disclosure.

Figure 8A:
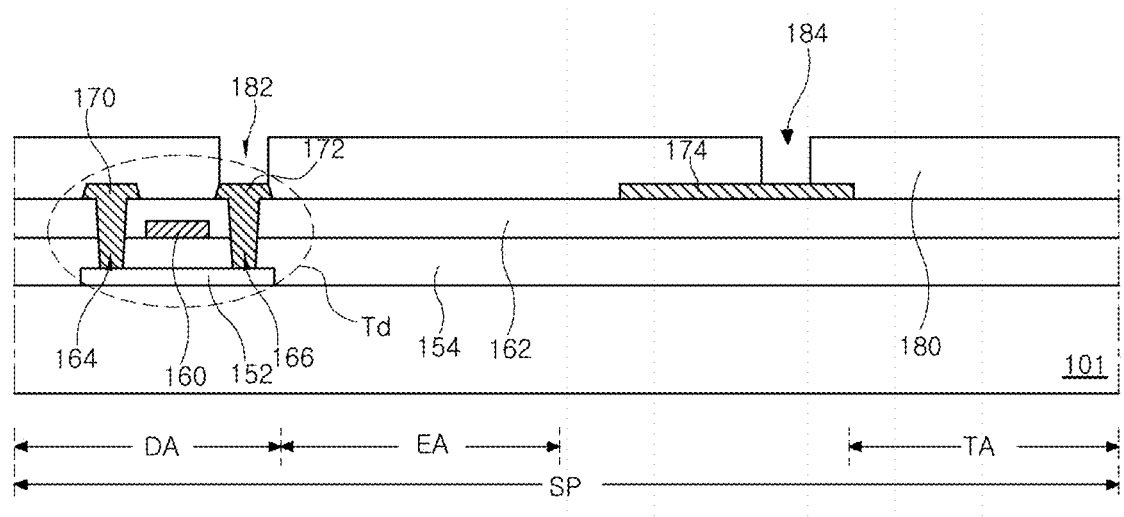
FIGS. 8A to 8G are schematic cross-sectional views showing a fabricating process of a transparent EL display device according to an embodiment of the present invention.

As shown in FIG. 8A, the driving TFT Td and the connection line 174 are formed on the substrate 101, and the passivation layer 180 including the drain electrode 182 and the first connection contact hole 184 are formed to cover the driving TFT Td and the connection line 174. A portion of the driving TFT Td and a portion of the connection line 174 are exposed through the drain contact hole 182 and the first connection contact hole 184, respectively.

More specifically, a semiconductor material is deposited on the substrate 101 and patterned by a masking process to form the semiconductor layer 152.

Next, the gate insulating layer 154 of an insulating material is formed on the semiconductor layer 152 and over an entire surface of the substrate 101.

Next, a low resistance metallic material, such as Cu or Al, is deposited on the gate insulating layer 154 and patterned by a masking process to form the gate electrode 160 on the gate insulating layer 154. The gate electrode 160 may correspond to a center of the semiconductor layer 152 and may be connected to the switching TFT.

Next, an insulating material layer is formed on the gate electrode 160 and patterned by a masking process to form the interlayer insulating layer 162 having the first and second contact holes 164 and 166. Both sides of the semiconductor layer 152 are exposed by the first and second contact holes 164 and 166, respectively.

Next, a low resistance metallic material, such as Cu or Al, is deposited on the interlayer insulating layer 162 and patterned by a masking process to form the source electrode 162, the drain electrode 172 and the connection line 174 on the interlayer insulating layer 162.

The source electrode 170 and the drain electrode 172 are spaced apart from each other with respect to the gate electrode 160 and respectively contact both sides of the semiconductor layer 152 through the first and second contact holes 164 and 166.

The semiconductor layer 152, the gate electrode 160, the source electrode 170 and the drain electrode 172 constitute the driving TFT Td.

Next, an insulating material layer is formed on the driving TFT Td and the connection line 174 and patterned by a masking process to form the passivation layer 180 having the drain contact hole 182 and the first connection contact hole 184.

Figure 8B:
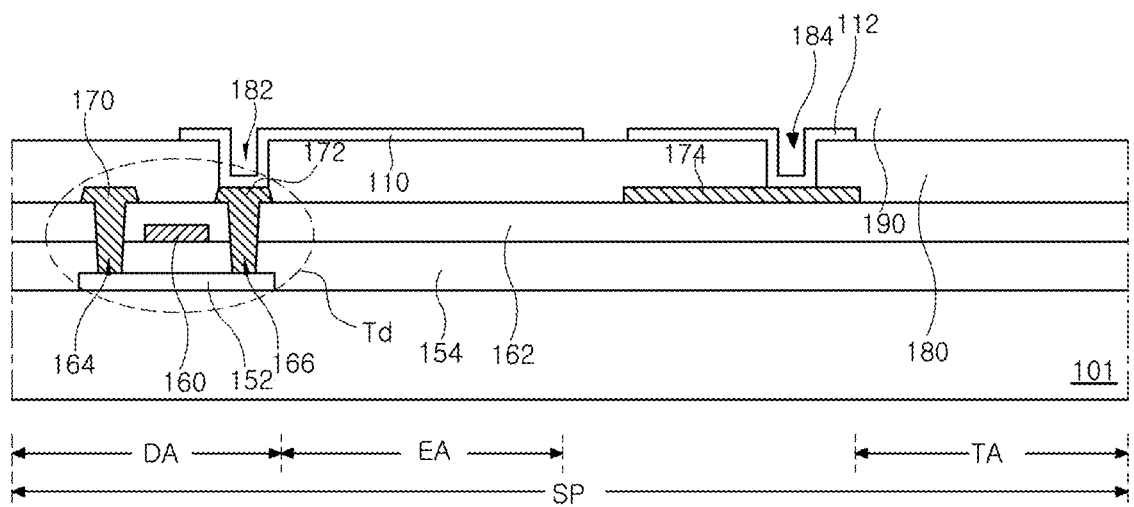

Next, as shown in FIG. 8B, a transparent conductive material is deposited on the passivation layer 180 and patterned by a masking process to form the first electrode 110 in the emission area (EA) and the connection pattern 112 corresponding to the connection line 112. The first electrode 110 is connected to the driving TFT Td through the drain contact hole 182, and the connection pattern 112 is connected to the connection line 174 through the first connection contact hole 184.

Figure 8C:
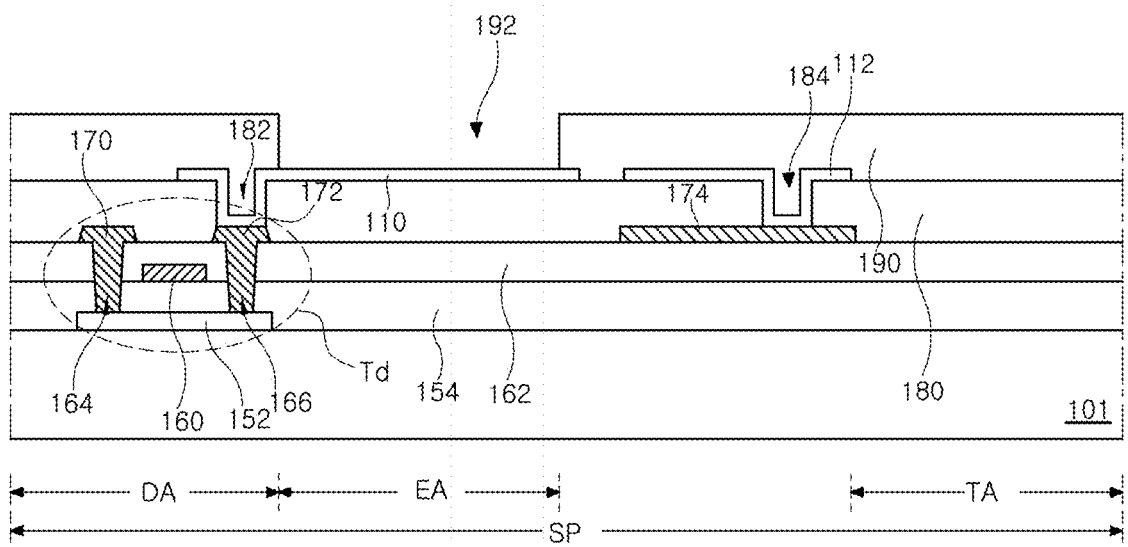

Next, as shown in FIG. 8C, an insulating material layer is formed and patterned by a masking process to form the bank 190 having the opening 192 in the emission area (EA). Namely, the bank 190 covers the connection pattern 112 and an edge of the first electrode 110.

Figure 8D:
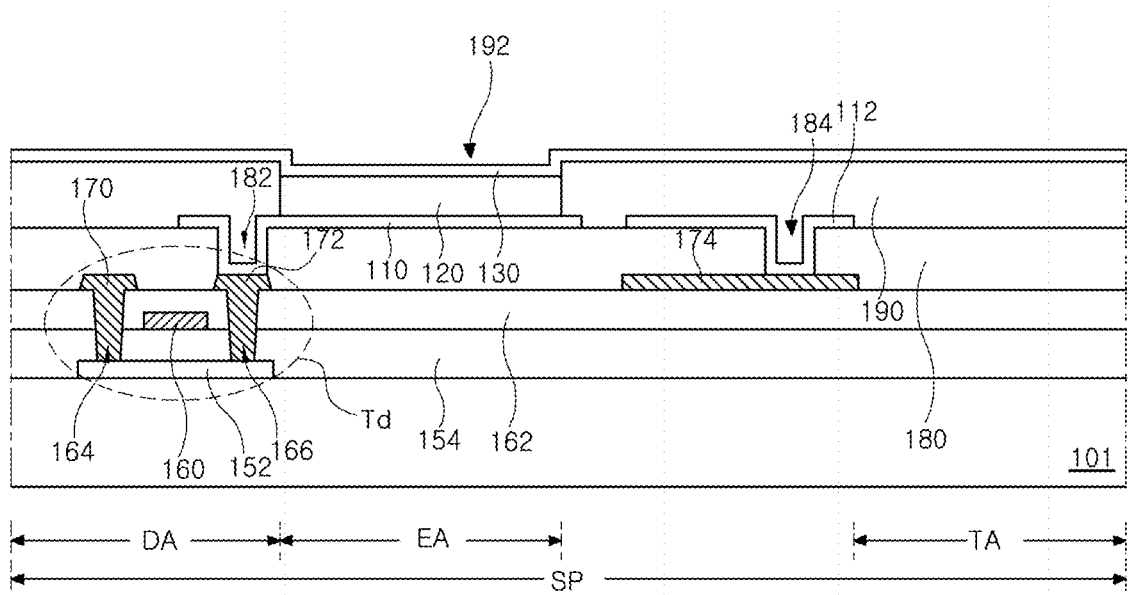

Next, as shown in FIG. 8D, the emitting material layer 120 is formed on the first electrode 110 in the emission area (EA), and the electron auxiliary layer 130 is formed on the emitting material layer 120 and the bank 190 to cover an entire surface of the display area including the emission area (EA) and the transparent area (TA). The electron auxiliary layer 130 includes the phase-transition optical isomer compound in Formula 1.

Although not shown, at least one of a hole injection layer and a hole transporting layer may be formed on the first electrode 110 before the emitting material layer 120 is formed.

Figure 8E:
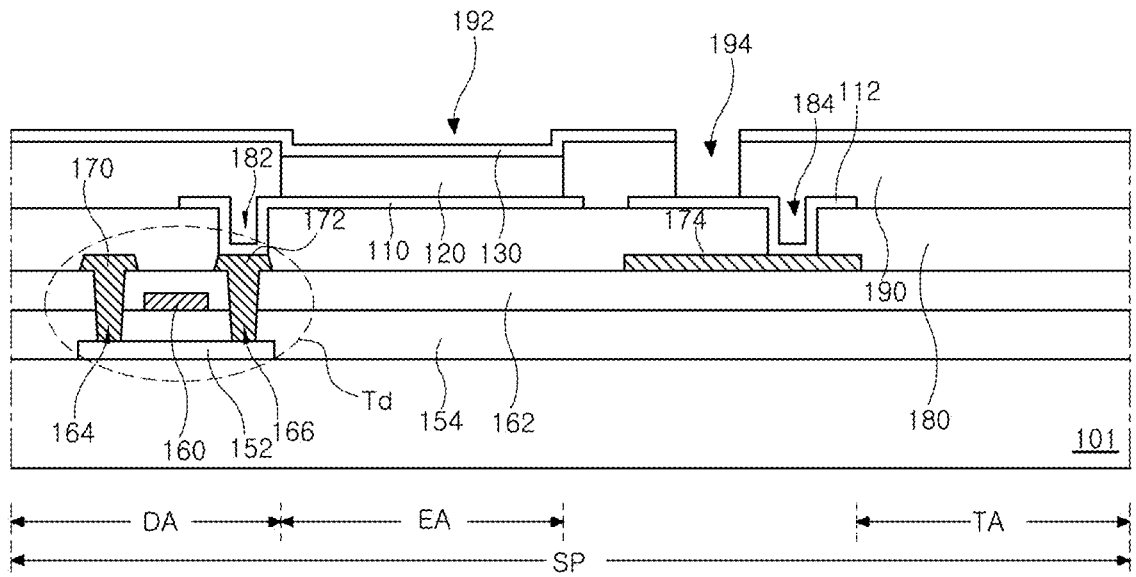

Next, as shown in FIG. 8E, the electron auxiliary layer 130 and the bank 190 corresponding to the connection pattern 112 are removed (etched) such that the second connection contact hole 194 exposing the connection pattern 112 is formed.

Figure 8F:
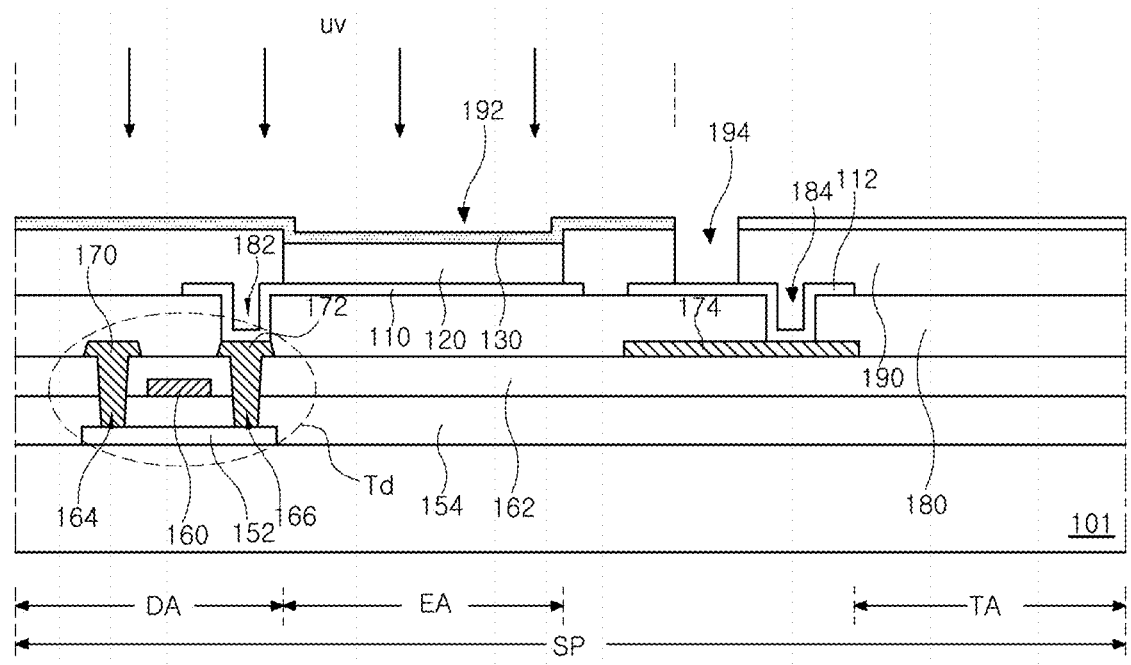

Next, as shown in FIG. 8F, ultraviolet rays irradiate the electron auxiliary layer 130 in the emission area (EA) such that the phase-transition optical isomer compound of the electron auxiliary layer 130 in the emission area (EA) is transited into the glassy phase. In contrast, since the ultraviolet rays do not irradiate the electron auxiliary layer 130 in the transparent area (TA), the rubbery phase of the phase-transition optical isomer compound of the electron auxiliary layer 130 in the transparent area TA is maintained.

Figure 8G:
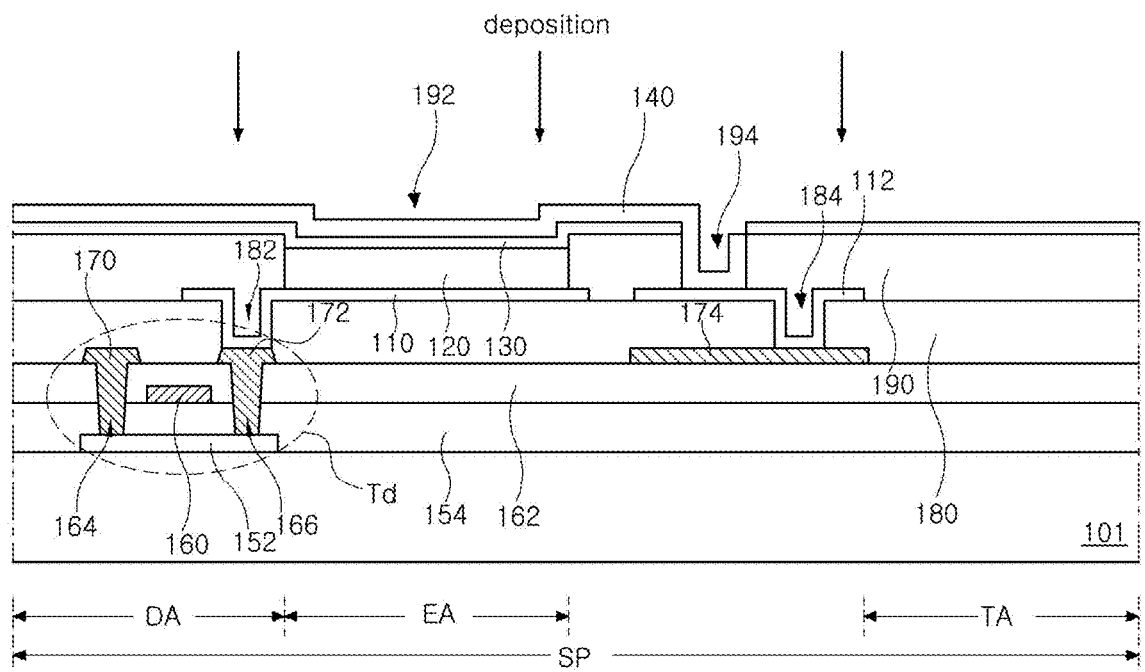

Next, as shown in FIG. 8G, a metal deposition process is performed onto an entire surface of the display area in the substrate 101 such that the second electrode 140 contacting the electron auxiliary layer 130 in the emission area (EA) is formed.

Since the phase-transition optical isomer compound of the electron auxiliary layer 130 in the transparent area (TA) exhibits the rubbery phase, the metal is not deposited in the transparent area (TA) and the second electrode 140 is not formed in the transparent area (TA). Namely, since the phase-transition optical isomer compound of the electron auxiliary layer 130 exhibits the glassy phase in the emission area (EA) and the rubbery phase in the transparent area (TA), the second electrode 140 is selectively formed in the emission area (EA).

In contrast, the electron auxiliary layer 130 in in correspondence with the second connection contact hole 194 is removed, and the second electrode 140 is formed in the second connection contact hole 194 such that the second electrode 140 is connected to the connection line 174 through the connection pattern 112.

In FIG. 8E, the phase-transition optical isomer compound in Formula 1 is deposited. In FIG. 8F, ultraviolet rays irradiate the emission area (EA).

Alternatively, the phase-transition optical isomer compound exhibiting the glassy phase as the compound in Formula 3 may be deposited to form the electron auxiliary layer 130, and the visible rays may irradiate the transparent area (TA). In this instance, the glassy phase in the phase-transition optical isomer compound of the electron auxiliary layer 130 is maintained in the emission area (EA) and is transited into the rubbery phase in the transparent area (TA) such that the second electrode 140 is selectively deposited onto the emission area (EA) except for the transparent area (TA).

Since the electron auxiliary layer 130 includes the phase-transition optical isomer compound, which is capable of transitioning between the glassy phase and the rubbery phase by light irradiation and has an electron transporting property and/or an electron injection property, the second electrode 140 is selectively deposited onto the emission area (EA) except for the transparent area (TA) without a masking process.

Accordingly, the transmittance decrease of the transparent EL display device 100 by the second electrode 140 is prevented without disadvantages in the fabricating process and the production cost.

Figure 9:
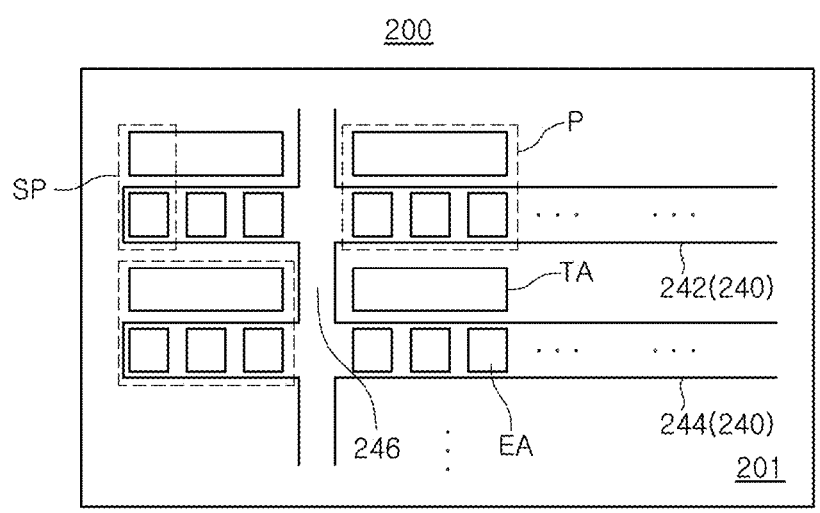
FIG. 9 is a schematic planar view of a transparent EL display device according to another embodiment of the present disclosure.

FIG. 9 is a schematic plane view of a transparent EL display device according to a second embodiment of the present disclosure.

As shown in FIG. 9, the transparent EL display device 200 includes a plurality of sub-pixel regions (SP) defined on a substrate 210 and arranged along a first direction and a second direction. Each of the plurality of sub-pixel regions (SP) includes an emission area (EA) and a transparent area (TA). Each sub-pixel region (SP) further includes a driving area (not shown).

For example, some of the plurality of sub-pixel regions (SP) that arrange along the first direction may constitute a pixel region (P). The pixel region (P) may include red, green and blue sub-pixel regions (SP).

In the emission area (EA) of the sub-pixel region (SP), an emitting diode (not shown) is disposed. For example, the emitting diode may include a first electrode, an emitting layer, an electron auxiliary layer and a second electrode 240.

As described below, the electron auxiliary layer includes a phase-transition optical isomer compound and transfers an electron from the second electron 240 into the emitting layer. Since a conductive material for the second electrode 240 is capable of being selectively deposited due to the electron auxiliary layer, the second electrode 240 is deposited in a desired area without a masking process.

The second electrode 240 corresponds to the emission area (EA) of the pixel regions (P) arranged along the first direction. Namely, in each pixel region (P) or each sub-pixel region (SP), the second electrode 240 is formed in the emission area (EA) except for the transparent area (TA). Accordingly, the sub-pixel region (SP) has a first width w1 in the second direction, and the second electrode 240 has a second width w2, which is smaller than the first width w1, in the second direction.

The second electrode 240 includes a plurality of electrode patterns 242 and 244 spaced apart from each other along the second direction. Namely, a first electrode pattern 242 corresponds to a first pixel row, and a second electrode pattern 244 corresponds to a second pixel row being spaced apart from the first pixel row along the second direction.

Accordingly, in the second direction, the sub-pixel region (SP) has the first width w1, and each of the first and second electrode patterns 242 and 244 has the second width w2 being smaller than the first width w1.

A bridge pattern 246 for electrically connecting the first and second electrode patterns 242 and 244 may be formed between the pixel regions (P) arranged along the first direction. Namely, one end of the bridge pattern 246 extends from (or contacts) one of the first electrode pattern 242 and the second electrode pattern 244, and the other one of the bridge pattern 246 extends from (or contacts) the other one of the first electrode pattern 242 and the second electrode pattern 244. The second electrodes 240, which respectively correspond to the first and second pixel rows and are spaced apart from each other, may be electrically connected to each other by the bridge pattern 246. The bridge pattern 246 may be formed at the same layer and formed of the same material as the second electrode 240.

In the transparent EL display device 200 of the present disclosure, since the second electrode 240 is not presented in the transparent area TA of the sub-pixel region (SP) and the pixel region (P), the problem of the transmittance decrease in the display area by the second electrode is prevented.

In addition, since the second electrode 240 is selectively formed in the emission area (EA) except for the transparent area (TA) by the electron auxiliary layer, which includes the phase-transition optical isomer compound, without a masking process, the problems of the fabricating process and the production costs are prevented.

Moreover, since the second electrodes 240 spaced apart from each other are electrically connected by the bridge pattern 246, there is no problem in applying voltage to the second electrodes 240.

Furthermore, since the electron auxiliary layer 130 (of FIG. 4) includes the phase-transition optical isomer compound, which is capable of transitioning between the glassy phase and the rubbery phase by light irradiation and has an electron transporting property and/or an electron injection property, the second electrode 240 is selectively deposited onto the emission area (EA) except for the transparent area (TA) without a masking process.

Accordingly, the transmittance decrease of the transparent EL display device 200 by the second electrode 240 is prevented without disadvantages in the fabricating process and the production costs.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A phase-transition optical isomer compound of formula:

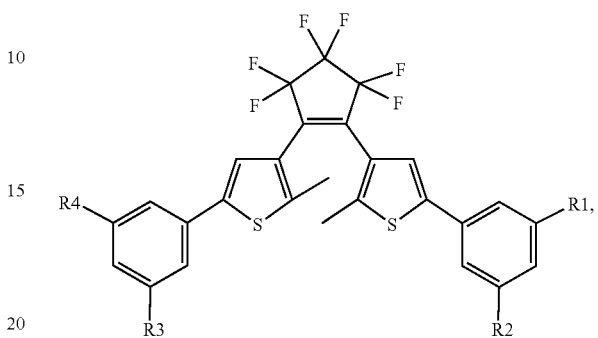

wherein each of R1 to R4 is independently selected from a heteroaromatic group containing a nitrogen atom.

2. The phase-transition optical isomer compound according to claim 1, wherein the phase-transition optical isomer compound is selected from the group consisting of:

compound 1

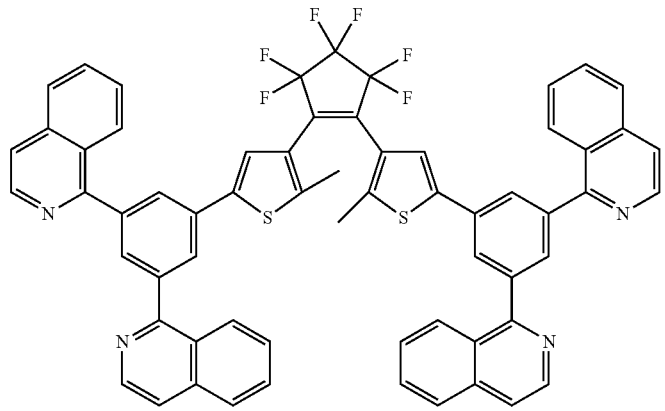

compound 2

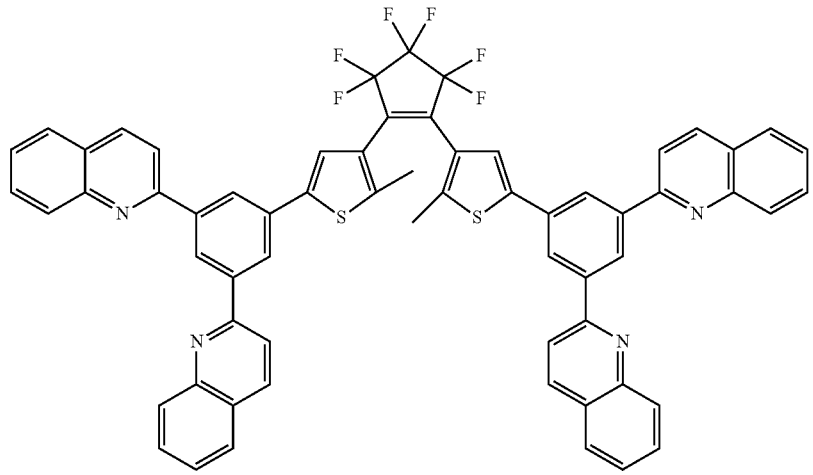

-continued

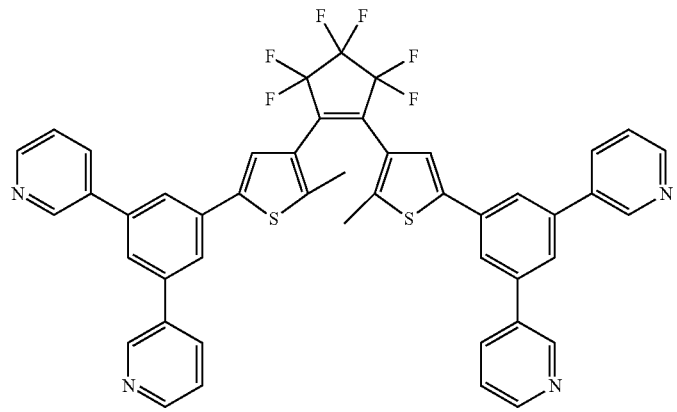

compound 3

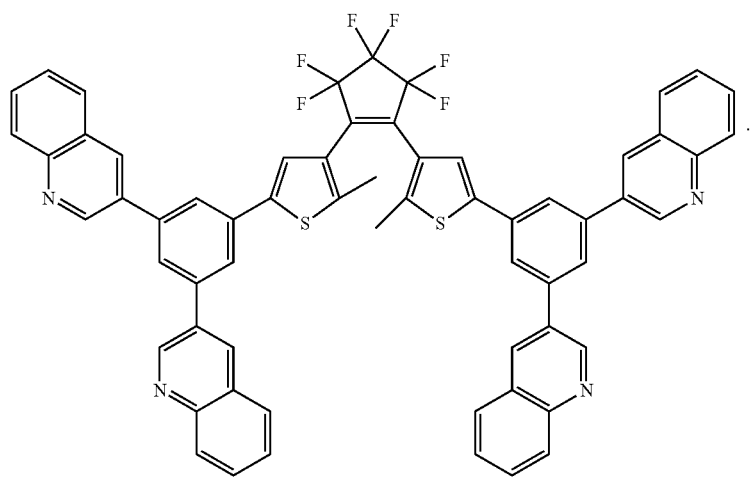

compound 4

3. The phase-transition optical isomer compound according to claim 1, wherein a difference between a glass temperature in a rubbery phase of the phase-transition optical isomer compound and a glass temperature in a glassy phase of the phase-transition optical isomer compound is between about 100 to 300° C.

4. The phase-transition optical isomer compound according to claim 1, wherein each of R1 to R4 is independently selected from pyridyl and quinolinyl.

5. The phase-transition optical isomer compound according to claim 1, wherein the phase-transition optical isomer compound exhibits a rubbery phase when a visible light is irradiated, and
wherein the phase-transition optical isomer compound exhibits a glassy phase when a ultraviolet ray is irradiated.

6. The phase-transition optical isomer compound according to claim 1, wherein the phase-transition optical isomer compound has a lowest unoccupied molecular orbital level of −2.6 to −2.1 eV and a highest occupied molecular orbital level of −6.2 to −6.0 eV.

7. The phase-transition optical isomer compound according to claim 1, wherein the phase-transition optical isomer compound comprises a compound in Formula 1 in a rubbery phase

[Formula 1]

compound 1

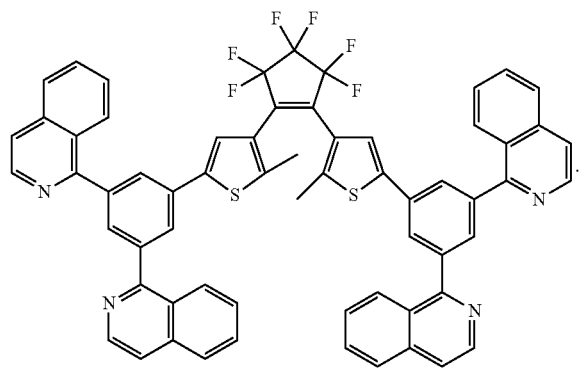

8. The phase-transition optical isomer compound according to claim 1, wherein the phase-transition optical isomer compound comprises a compound in Formula 2 in glassy phase:
[Formula 2]
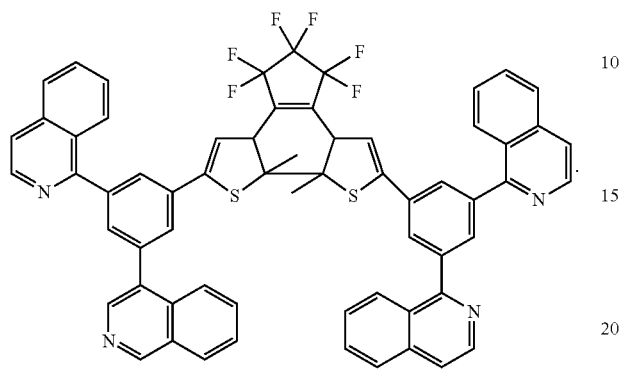
* * * * *